(12) United States Patent
Liu et al.

(10) Patent No.: US 11,789,005 B2
(45) Date of Patent: Oct. 17, 2023

(54) DEVICE AND METHOD FOR DETERMINING DEGRADATION RATE OF BIODEGRADABLE POLYMERS IN SOIL

(71) Applicants: NORTH UNIVERSITY OF CHINA, Taiyuan (CN); SHANXI ZHONGBEI NEW MATERIAL TECHNOLOGY CO., LTD., Taiyuan (CN)

(72) Inventors: Yaqing Liu, Taiyuan (CN); Taian Chen, Taiyuan (CN); Yang Xiang, Taiyuan (CN); Guizhe Zhao, Taiyuan (CN)

(73) Assignees: NORTH UNIVERSITY OF CHINA, Taiyuan (CN); SHANXI ZHONGBEI NEW MATERIAL TECHNOLOGY CO., LTD., Taiyuan (CN)

( * ) Notice: Subject to any disclaimer, the term of this patent is extended or adjusted under 35 U.S.C. 154(b) by 0 days.

(21) Appl. No.: 17/581,918

(22) Filed: Jan. 22, 2022

(65) Prior Publication Data

US 2022/0146489 A1  May 12, 2022

(30) Foreign Application Priority Data

Nov. 23, 2021 (CN) .......................... 202111395924.2

(51) Int. Cl.
*G01N 33/44* (2006.01)
*G01N 1/24* (2006.01)
(Continued)

(52) U.S. Cl.
CPC ............. *G01N 33/442* (2013.01); *C12M 1/00* (2013.01); *C12M 1/02* (2013.01); *C12M 1/04* (2013.01);
(Continued)

(58) Field of Classification Search
CPC .......... G01N 1/24; G01N 1/38; G01N 33/442; C12M 1/00; C12M 1/02; C12M 1/04; C12M 1/12
(Continued)

(56) References Cited

U.S. PATENT DOCUMENTS

2022/0146489 A1\* 5/2022 Liu ...................... G01N 33/442

FOREIGN PATENT DOCUMENTS

| CN | 201828552 U | \* | 5/2011 |
| CN | 201828552 U | | 5/2011 |

(Continued)

OTHER PUBLICATIONS

Lloyd L. Falk et al, Factors Affecting the Direct Oxygen Utilization Method, Sewage Works Journal, vol. 19, No. 6 (Nov. 1947), pp. 1000-1006 (Year: 1947).\*

(Continued)

*Primary Examiner* — Stephanie E Bloss
*Assistant Examiner* — Kevin C Butler

(57) ABSTRACT

A device for determining degradation rate of biodegradable polymers in soil, including a micro compressed air pump, a first $CO_2$ absorption vessel filled with dry soda lime or an aqueous strong alkali solution, a $CO_2$ indicator vessel filled with a barium hydroxide solution, a hollow leaching device, a second $CO_2$ absorption vessel and a third $CO_2$ absorption vessel connected in sequence through connecting pipes. A top of the hollow leaching device is provided with an end cover. An external water distributor filled with a leaching solution and a mechanical stirring device is arranged above the end cover. The external water distributor is in communication with an inner cavity of the hollow leaching device through a pipeline. A stirring shaft of the mechanical stirring device extends into the inner cavity. A stirring shaft is provided with a stirring paddle.

5 Claims, 1 Drawing Sheet

(51) Int. Cl.
  *G01N 1/38*     (2006.01)
  *C12M 1/00*     (2006.01)
  *C12M 1/02*     (2006.01)
  *C12M 1/12*     (2006.01)
  *C12M 1/04*     (2006.01)

(52) U.S. Cl.
  CPC ............... *C12M 1/12* (2013.01); *G01N 1/24* (2013.01); *G01N 1/38* (2013.01)

(58) Field of Classification Search
  USPC ........................................................ 73/23.2
  See application file for complete search history.

(56) References Cited

FOREIGN PATENT DOCUMENTS

| | | | | |
|---|---|---|---|---|
| CN | 208648862 U | * | 3/2019 | |
| CN | 111157440 A | * | 5/2020 | |
| CN | 111157440 A |   | 5/2020 | |
| CN | 113755310 A | * | 12/2021 | |
| CN | 113917088 A | * | 1/2022 | |
| CN | 114280271 A | * | 4/2022 | ............... G01N 1/24 |
| CN | 114544859 A | * | 5/2022 | |

OTHER PUBLICATIONS

U.Pagga et al., Determination of Tee Aerobic Biodegradability of Polymeric Material in a Laboratory Controlled Composting Test, Chemosphere, vol. 31, Nos. 11112, pp. 44754487, 1995 (Year: 1995).*

* cited by examiner

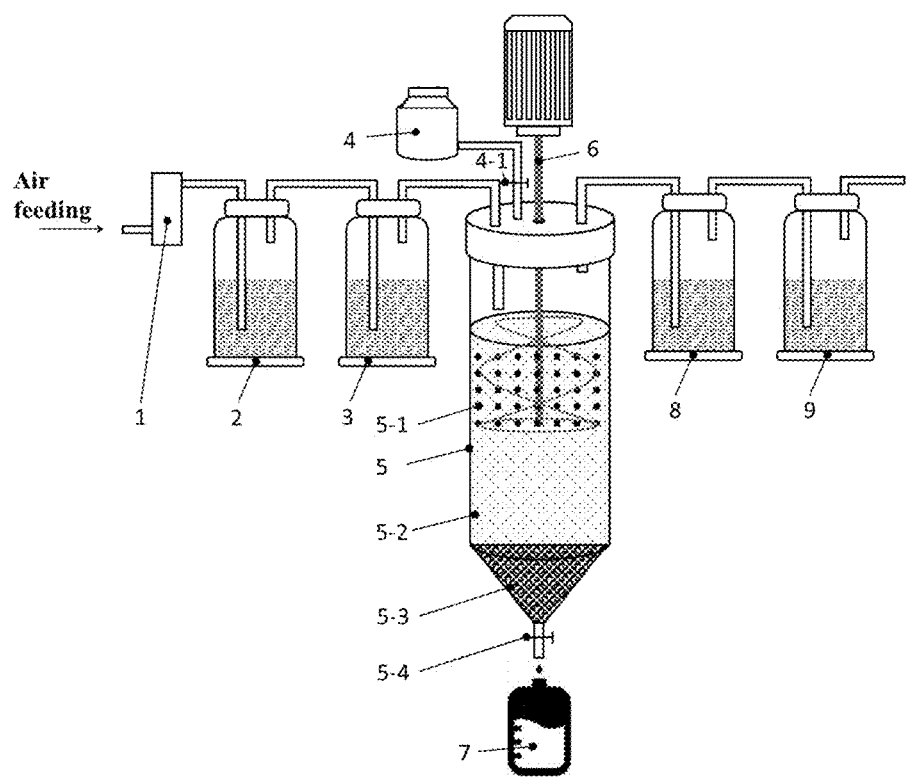

DEVICE AND METHOD FOR DETERMINING DEGRADATION RATE OF BIODEGRADABLE POLYMERS IN SOIL

CROSS-REFERENCE TO RELATED APPLICATIONS

This application claims the benefit of priority from Chinese Patent Application No. 202111395924.2, filed on Nov. 23, 2021. The content of the aforementioned application, including any intervening amendments thereto, is incorporated herein by reference in its entirety.

TECHNICAL FIELD

This application relates to biodegradable polymers, and more particularly to a device and method for determining a degradation rate of a biodegradable polymer in soil.

BACKGROUND

In order to alleviate the white pollution caused by non-degradable polymers, some environmentally-friendly biodegradable polymers, such as cellulose and polybutylene succinate (PBS), have been recommended to replace those traditional non-degradable plastics. These biodegradable polymers generally carry a large number of readily-hydrolyzed groups, such as ester, amide and hydroxyl groups, in the molecular backbone or side chain, which can be recognized by microorganisms, so as to allow the polymers to be completely degraded and converted into $CO_2$, water, mineralized inorganic salts and microbial biomass within a certain period of time.

Currently, the waste biodegradable polymers are still most-frequently treated by landfilling. Considering the increasingly extensive applications of biodegradable polymers in the agricultural field, a large number of discarded biodegradable polymers will inevitably penetrate into the soil. At present, the biodegradation rate or biodegradability of materials in soil is generally characterized by weight loss or changes in the material properties, including chemical composition, molecular structure, mechanical properties, molecular weight, and surface morphology. By contrast, the macroscopic indicator "weight loss" is readily measurable for the evaluation of the biodegradation rate. Additionally, the amount of $CO_2$ release can also be employed as an index to determine the degradation rate of the biodegradable polymers in soil. Unfortunately, with respect to the existing devices for measuring the biodegradability and degradation rate of the biodegradable polymers, the degradation process of the polymers occurs in a closed environment, which will result in the gradual accumulation and eventual saturation of the released small-molecule organic substance, significantly influencing the subsequent determination of the biodegradability and degradation rate.

SUMMARY

In view of the defects of complex structure, high cost and poor determination accuracy in the existing devices for determining a degradation rate and a biodegradability of biodegradable polymers, this disclosure provides a device and method for determining a degradation rate of a biodegradable polymer in soil.

Technical solutions of this application are described as follows.

In a first aspect, the present disclosure provides a device for determining a degradation rate of a biodegradable polymer in soil, comprising:

a micro compressed air pump;
a first $CO_2$ absorption vessel;
a $CO_2$ indicator vessel;
a hollow leaching device;
a second $CO_2$ absorption vessel; and
a third $CO_2$ absorption vessel;

wherein the micro compressed air pump, the first $CO_2$ absorption vessel, the $CO_2$ indicator vessel, the hollow leaching device, the second $CO_2$ absorption vessel and the third $CO_2$ absorption vessel are connected in sequence through a connecting pipe; a top of the hollow leaching device is provided with an end cover; an external water distributor and a mechanical stirring device are arranged above the end cover; the external water distributor is in communication with an inner cavity of the hollow leaching device through a pipeline; a stirring shaft of the mechanical stirring device extends into the inner cavity of the hollow leaching device; a portion of the stirring shaft in the hollow leaching device is provided with a stirring paddle; the first $CO_2$ absorption vessel is filled with dry soda lime or a first aqueous strong alkali solution; the $CO_2$ indicator vessel contains a barium hydroxide solution; the external water distributor contains a leaching solution with a preset pH; an upper part of the inner cavity of the hollow leaching device is filled with a certain mass of soil as a leaching zone; a bottom of the inner cavity of the hollow leaching device has an inverted cone shape, and is filled with quartz sand particles as a filter zone; a bottom of the filter zone is provided with a water outlet; a lower part of the water outlet is provided with a leachate collecting container; and each of the second $CO_2$ absorption vessel and the third $CO_2$ absorption vessel is filled with a second aqueous strong alkali solution; an air inlet of the connecting pipe is arranged above a liquid level, and an air outlet of the connecting pipe is arranged below the liquid level.

In an embodiment, the pipeline communicating the external water distributor with the inner cavity of the hollow leaching device is provided with a liquid inlet control valve.

In an embodiment, the hollow leaching device is a hollow cylindrical leaching device; and the water outlet of the hollow leaching device is provided with a leachate control valve.

In an embodiment, a connection between the stirring shaft of the mechanical stirring device and the end cover of the hollow leaching device is provided with a mechanical seal ring.

The micro compressed air pump, the first $CO_2$ absorption vessel, and the $CO_2$ indicator vessel form an air input zone, where the micro compressed air pump is configured to feed an airflow into the device continuously and stably; the first $CO_2$ absorption vessel is filled with dry soda lime or the aqueous strong alkali solution to absorb $CO_2$ in the airflow; and the $CO_2$ indicator vessel contains the barium hydroxide solution to determine whether there is $CO_2$ mixed in the airflow by its turbidity.

The external water distributor is configured as a water inlet zone, which is filled with the leaching solution with a preset pH to realize a continuous and stable liquid feeding or an intermittent liquid feeding through the external liquid inlet control valve.

The hollow leaching device and the mechanical stirring device together form a leaching zone. The upper part of the inner cavity of the hollow leaching device is filled with a certain mass of soil to biologically degrade the biodegradable polymer. The filter zone at the bottom of the inner cavity of the hollow leaching device is designed into an inverted cone shape and is filled with quartz sand particles to filter the leachate to prevent the soil and solid undegraded biodegradable polymer from flowing out. The lower end of the leaching device is provided with an outlet and the leachate control valve to control the discharge of the leachate. The connection between the stirring shaft of the mechanical stirring device and the end cover of the hollow leaching device is provided with a mechanical seal ring. The mechanical stirring device is configured to evenly mix the biodegradable polymer and degradation products with the soil and promote the gas exchange between the soil and the upper air layer.

The leachate collecting container is a leachate collecting zone, which configured to collect the leachate.

The second $CO_2$ absorption vessel and the third $CO_2$ absorption vessel, both containing an aqueous strong alkali solution, together form a gas collecting zone to collect the $CO_2$ gas generated from the biodegradation and mineralization of the biodegradable polymer.

In a second aspect, the present disclosure provides a method for determining the degradation rate of the biodegradable polymer in soil using the above device, comprising:

(S1) choosing a soil and a leaching solution according to an actual test objective and experimental conditions; evenly mixing a biodegradable polymer sample to be tested and a certain mass of the soil followed by feeding to the hollow leaching device;

(S2) turning on the micro compressed air pump and the mechanical stirring device, and opening the liquid inlet control valve and the leachate control valve; and setting an air inlet flow rate, a liquid inlet flow rate, a stirring speed, and a liquid outlet flow rate according to the actual test objective and experimental conditions to allow the biodegradable polymer sample to be biodegraded in the soil under a set condition;

(S3) regularly collecting a leachate in the leachate collecting container and the strong alkali solution in the second $CO_2$ absorption vessel and the third $CO_2$ absorption vessel; measuring a carbon content in the leachate and the strong alkali solution using an organic carbon analyzer or by an acid-base titration; wherein during a biodegradation process, if the barium hydroxide solution in the $CO_2$ indicator vessel in an air input zone becomes turbid, it is required to replace the strong alkali solution in the first $CO_2$ absorption vessel and the barium hydroxide solution in the $CO_2$ indicator vessel;

(S4) repeating step (S3) until the biodegradable polymer sample is completely degraded or the degradation rate meeting the test objective is reached; and (S5) based on the measured data, determining the biodegradability and the degradation rate of the biodegradable polymer sample in the soil according to equation (1) shown as follows:

$$D_t = \frac{(m_{slt} + m_{sct}) - (m_{blt} + m_{bct})}{m_s w_c} \times 100; \quad (1)$$

wherein $D_t$ is a degradation rate of the biodegradable polymer sample in the soil from a beginning of the test to time t, expressed by %;

$m_{slt}$ is a carbon content of all leachate samples collected from a treatment of the biodegradable polymer sample from the beginning of the test to the time t, with a unit of mg;

$m_{sct}$ is a carbon content of all $CO_2$ released from the biodegradation process of the biodegradable polymer sample from the beginning of the test to the time t, with a unit of mg;

$m_{blt}$ is a carbon content of all leachate samples collected in a blank treatment, i.e., treatment without adding the biodegradable polymer sample from the beginning of the test to the time t, with a unit of mg;

$m_{bct}$ is a carbon content of all $CO_2$ released in the blank treatment from the beginning of the test to the time t, with a unit of mg;

$m_s$ is a total mass of the biodegradable polymer sample added at the beginning of the test, with a unit of mg; and $w_c$ is a carbon content of the biodegradable polymer sample added at the beginning, expressed by %, wherein the carbon content is calculated from its chemical molecular formula or tested by an organic carbon analyzeror or an elemental analyzer.

Compared with the prior art, this application has the following beneficial effects.

(1) The device and method provided herein can overcome the limitations in the prior art that the soil culture system can only exchange gas with the outside, and can realistically simulate the biodegradation process of the biodegradable polymers under a natural soil environment, so as to precisely and reliably evaluate the biodegradability of the biodegradable polymer under the natural soil environment.

(2) The device and method provided herein overcome the one-sidedness and limitation in the existing biodegradability characterization methods by mineralization and degradation rate characterizing through $CO_2$ release, and clarify the carbon transfer and transformation in the degradation of the biodegradable polymers in the real soil-atmosphere system.

(3) The method provided herein can not only simplify the sampling and analysis of the soil, leachate and gas, but also avoid using a complicated analysis device in the prior art, so as to reduce the testing cost, simplify the testing process and improve the testing accuracy of the biodegradability of the biodegradable polymers in soil.

BRIEF DESCRIPTION OF THE DRAWINGS

This FIGURE is a structural diagram of a device for determining a degradation rate of a biodegradable polymer in soil according to an embodiment of this application;

in the drawing, 1: micro compressed air pump; 2: first $CO_2$ absorption vessel; 3: $CO_2$ indicator vessel; 4: external water distributor; 4-1: liquid inlet control valve; 5: hollow leaching device; 5-1: biodegradable polymer sample to be tested; 5-2: soil; 5-3: quartz sand particle; 5-4: leachate control valve; 6: mechanical stirring device; 7: leachate collecting container; 8: second $CO_2$ absorption vessel; and 9: third $CO_2$ absorption vessel.

DETAILED DESCRIPTION OF EMBODIMENTS

This application will be described in detail below with reference to the embodiments and accompanying drawings.

Embodiment 1

As shown in the FIGURE, a device for determining a degradation rate of a biodegradable polymer in soil provided herein includes an air input zone, a water inlet zone, a leaching zone, a leachate collecting zone and a gas collecting zone. The air input zone includes a micro compressed air pump 1 configured to continuously and stably feed an airflow into the device, a first $CO_2$ absorption vessel 2 filled with dry soda lime or the aqueous strong alkali solution to absorb $CO_2$ in the airflow, and a $CO_2$ indicator vessel 3 containing a barium hydroxide solution to determine whether there is $CO_2$ mixed in the airflow by its turbidity. The water inlet zone is an external water distributor 4 containing a leaching solution with a preset pH value to realize a continuous and stable liquid feeding or an intermittent liquid feeding through the external liquid inlet control valve 4-1. The leaching zone is formed by a hollow leaching device 5 together with a mechanical stirring device 6. An upper part of an inner cavity of the hollow leaching device 5 is filled with a certain mass of soil 5-2 to biologically degrade a biodegradable polymer sample 5-1 to be tested in soil. A filter zone at a bottom of the inner cavity of the hollow leaching device 5 is designed into an inverted cone shape and is filled with quartz sand particles 5-3 to filter a leachate to prevent the soil and solid undegraded biodegradable polymer from flowing out. An upper part of the hollow cylindrical leaching device is provided with the mechanical stirring device 6. A connection between the stirring shaft of the mechanical stirring device and the end cover of the hollow leaching device is provided with a mechanical seal ring. The mechanical stirring device 6 is configured to evenly mix the biodegradable polymer and degradation products with the soil and promote the gas exchange between the soil and the upper air layer. A lower end of the hollow leaching device 5 is provided with an outlet and a leachate control valve 5-4 to control the discharge of the leachate. The leachate collecting zone is formed by a leachate collecting container 7, which configured to collect the leachate. The gas collecting zone includes a second $CO_2$ absorption vessel 8 and a third $CO_2$ absorption vessel 9, both of which contain an aqueous strong alkali solution to collect the $CO_2$ gas generated from the biodegradation and mineralization of the biodegradable polymer.

Embodiment 2

A method for determining a degradation rate of a biodegradable polymer in soil using the device in Embodiment 1 is provided, which includes the following steps.

(S1) A soil and a leaching solution corresponding to an actual test objective and experimental conditions are chosen to obtain desired biodegradation conditions of the biodegradable polymer, and then a biodegradable polymer sample 5-1 to be tested and a certain mass of the soil are mixed evenly, and the device is assembled according to the FIGURE.

(S2) A micro compressed air pump 1 and a mechanical stirring device 6 are turned on, and a liquid inlet control valve 4-1 and a leachate control valve 5-4 are opened. An air inlet flow rate, a liquid inlet flow rate, a stirring speed, and a liquid outlet flow rate are set according to the actual test objective and experimental conditions to allow the biodegradable polymer sample to be biodegraded in the soil under a set condition.

(S3) A leachate in a leachate collecting container 7 and a strong alkali solution in a second $CO_2$ absorption vessel 8 and a third $CO_2$ absorption vessel 9 are collected regularly. Carbon contents in the leachate and the strong alkali solution are measured using an organic carbon analyzer or by an acid-base titration. During a biodegradation process, if a barium hydroxide solution in a $CO_2$ indicator vessel 3 in an air input zone becomes turbid, it is required to replace the strong alkali solution in a first $CO_2$ absorption vessel 2 and the barium hydroxide solution in a $CO_2$ indicator vessel 3.

(S4) Step (S3) is repeated until the biodegradable polymer sample is completely degraded or the degradation rate meeting the test objective is reached.

(S5) Based on a measured data, a biodegradability and the degradation rate of the biodegradable polymer sample in soil are determined according to equation (1) shown as follows;

$$D_t = \frac{(m_{slt} + m_{sct}) - (m_{blt} + m_{bct})}{m_s w_c} \times 100; \quad (1)$$

where $D_t$ is a degradation rate of the biodegradable polymer sample in the soil from a beginning of the test to time t, expressed by %;

$m_{slt}$ is a carbon content of all leachate samples collected from a treatment of the biodegradable polymer sample from the beginning of the test to the time t, with a unit of mg;

$m_{sct}$ is a carbon content of all $CO_2$ released from the biodegradation process of the biodegradable polymer sample from the beginning of the test to the time t, with a unit of mg;

$m_{blt}$ is a carbon content of all leachate samples collected in a blank treatment, i.e. treatment without adding the biodegradable polymer sample from the beginning of the test to the time t, with a unit of mg;

$m_{bct}$ is a carbon content of all $CO_2$ released in the blank treatment from the beginning of the test to the time t, with a unit of mg;

$m_s$ is a total mass of the biodegradable polymer sample added at the beginning of the test, with a unit of mg; and $w_c$ is a carbon content of the biodegradable polymer sample added at the beginning, expressed by %, wherein the carbon content is calculated from its chemical molecular formula or determined by an organic carbon analyzer or an elemental analyzer.

Based on the steps in the method provided above, in the biodegradability and biodegradation rate test of the biodegradable polymer in soil, all the samples have the same shape and size, and the air inlet flow rate, the liquid inlet flow rate, the stirring speed and the liquid outlet flow rate are the same too, which not only ensure the comparability of the degradation data, but also enable to choose different soils and leaching solutions to realize the biodegradability tests under different conditions.

Embodiment 3

A method for determining a degradation rate of a biodegradable polymer in soil using the device in Embodiment 1 is provided, which includes the following steps.

(S1) A biodegradability of a biodegradable cellulose in Taiyuan city (Shanxi, China) area is investigated. The cellulose powders containing 100 g of carbon is mixed evenly with 6 Kg of a soil sample collected from a suburban farmland in Taiyuan and air-dried and sieved to obtain a mixture. Then the mixture of the cellulose and soil is added into a leaching column with a diameter of 8 cm and a height of 1.2 m. A first $CO_2$ absorption vessel 2 is filled with a 20 wt % sodium hydroxide solution. A $CO_2$ indicator vessel 3 is filled with a 1 wt % barium hydroxide solution. A second $CO_2$ absorption vessel 8 a third $CO_2$ absorption vessel 9 are both filled with a 10 wt % sodium hydroxide solution. An external water distributor 4 is filled with deionized water with pH=7. The device is assembled according to the FIGURE.

(S2) A micro compressed air pump 1 and a mechanical stirring device 6 are turned on, and a liquid inlet control valve 4-1 and a leachate control valve 5-4 are opened. An air inlet flow rate is set at 0.1 L/h; a liquid inlet flow rate is set at 0.05 L/h; a stirring speed is set at 10 r/min; and a liquid outlet flow rate is set at 0.05 L/h.

(S3) A leachate in a leachate collecting container 7 and a strong alkali solution in the second $CO_2$ absorption vessel 8 and the third $CO_2$ absorption vessel 9 are collected on the $30^{th}$, $60^{th}$, $90^{th}$, $120^{th}$, $150^{th}$, $180^{th}$ and $210^{th}$ day of the test, respectively, and analyzed for a carbon content by means of an organic carbon analyzer. During a biodegradation process, if a barium hydroxide solution in the $CO_2$ indicator vessel 3 in the air input zone becomes turbid, it is required to replace the strong alkali solution in the first $CO_2$ absorption vessel 2 and the $CO_2$ indicator vessel 3.

(S4) According to the equation 1, the degradation rates of cellulose on the $30^{th}$, $60^{th}$, $90^{th}$, $120^{th}$, $150^{th}$, $180^{th}$ and $210^{th}$ days are determined to be 10%, 26%, 39%, 51%, 62%, 73% and 82%, respectively.

What is claimed is:

1. A device for determining a degradation rate of a biodegradable polymer in soil, comprising:
    a micro compressed air pump;
    a first $CO_2$ absorption vessel;
    a $CO_2$ indicator vessel;
    a hollow leaching device;
    a second $CO_2$ absorption vessel; a third $CO_2$ absorption vessel;
    an external water distributor;
    a mechanical stirring device; and
    a leachate collecting container;
    wherein the micro compressed air pump, the first $CO_2$ absorption vessel, the $CO_2$ indicator vessel, the hollow leaching device, the second $CO_2$ absorption vessel, and the third $CO_2$ absorption vessel are connected in sequence through a connecting pipe; a top of the hollow leaching device is provided with an end cover; the external water distributor and the mechanical stirring device are arranged above the end cover; the external water distributor is in communication with an inner cavity of the hollow leaching device through a connecting pipeline; a stirring shaft of the mechanical stirring device extends into the inner cavity of the hollow leaching device; the stirring shaft in the hollow leaching device is provided with a stirring paddle; the first $CO_2$ absorption vessel is filled with dry soda lime or a first aqueous strong alkali solution; the $CO_2$ indicator vessel contains a barium hydroxide solution; the external water distributor contains a leaching solution with a preset pH value; an upper part of the inner cavity of the hollow leaching device is filled with a certain mass of soil as a leaching zone; a bottom of the inner cavity of the hollow leaching device has an inverted cone shape and is filled with quartz sand particles as a filter zone; a bottom of the filter zone is provided with a water outlet; a lower part of the water outlet is provided with the leachate collecting container; each of the second $CO_2$ absorption vessel and the third $CO_2$ absorption vessel is filled with a second aqueous strong alkali solution; and an air outlet of a connecting pipe between the $CO_2$ indicator vessel and the hollow leaching device is arranged above a liquid level in the hollow leaching device.

2. The device of claim 1, wherein the connecting pipe communicating the external water distributor with the inner cavity of the hollow leaching device is provided with a liquid inlet control valve.

3. The device of claim 1, wherein the hollow leaching device is a hollow cylindrical leaching device; and the water outlet of the hollow leaching device is provided with a leachate control valve.

4. The device of claim 1, wherein a connection between the stirring shaft of the mechanical stirring device and the end cover of the hollow leaching device is provided with a mechanical seal ring.

5. A method for determining the degradation rate of the biodegradable polymer in soil using the device of claim 1, comprising
    (S1) choosing a soil and a leaching solution according to an actual test objective and experimental conditions; evenly mixing a biodegradable polymer sample to be tested and a certain mass of the soil followed by feeding to the hollow leaching device;
    (S2) turning on the micro compressed air pump and the mechanical stirring device, and opening a liquid inlet control valve and a leachate control valve; and setting an air inlet flow rate, a liquid inlet flow rate, a stirring speed, and a liquid outlet flow rate according to the actual test objective and experimental conditions to allow the biodegradable polymer sample to be biodegraded in the soil under a set condition;
    (S3) regularly collecting a leachate in the leachate collecting container and the second aqueous strong alkali solution in the second $CO_2$ absorption vessel and the third $CO_2$ absorption vessel; measuring carbon contents in the leachate and the second aqueous strong alkali solution using an organic carbon analyzer or by an acid-base titration; wherein during a biodegradation process, if the barium hydroxide solution in the $CO_2$ indicator vessel in an air input zone becomes turbid, it is required to replace the first aqueous strong alkali solution in the first $CO_2$ absorption vessel and the barium hydroxide solution in the $CO_2$ indicator vessel;
    (S4) repeating step (S3) until the biodegradable polymer sample is completely degraded or the degradation rate meeting the test objective is reached; and
    (S5) based on a measured data, determining a biodegradability and the degradation rate of the biodegradable polymer sample in the soil according to equation (1) shown as follows:

$$D_t = \frac{(m_{slt} + m_{sct}) - (m_{blt} + m_{bct})}{m_s w_c} \times 100; \tag{1}$$

wherein $D_t$ is a degradation rate of the biodegradable polymer sample in the soil from a beginning of the test to time t, expressed by %;
    $m^{slt}$ is a carbon content of all leachate samples collected from a treatment of the biodegradable polymer sample from the beginning of the test to the time t, with a unit of mg;
    $m_{sct}$ is a carbon content of all $CO_2$ released from the biodegradation process of the biodegradable polymer sample from the beginning of the test to the time t, with a unit of mg;
    $m_{blt}$ a carbon content of all leachate samples collected in a blank treatment from the beginning of the test to the time t, with a unit of mg;

$m_{bct}$ is a carbon content of all $CO_2$ released in the blank treatment from the beginning of the test to the time t, with a unit of mg;

$m_s$ is a total mass of the biodegradable polymer sample added at the beginning of the test to the time t, with a unit of mg; and $w_c$ is a carbon content of the biodegradable polymer sample added at the beginning, expressed by %, wherein the carbon content is calculated from a chemical molecular formula of the biodegradable polymer sample or determined by an organic carbon analyzer or an elemental analyzer.

* * * * *